United States Patent
Fuisz (10) Patent No.: US 8,568,777 B2
(45) Date of Patent: Oct. 29, 2013

(54) PACKAGED FILM DOSAGE UNIT CONTAINING A COMPLEXATE

(75) Inventor: Richard C. Fuisz, McLean, VA (US)

(73) Assignee: MonoSol Rx, LLC, Warren, NJ (US)

( * ) Notice: Subject to any disclaimer, the term of this patent is extended or adjusted under 35 U.S.C. 154(b) by 237 days.

(21) Appl. No.: 11/731,139

(22) Filed: Mar. 30, 2007

(65) Prior Publication Data

US 2008/0242736 A1 Oct. 2, 2008

(51) Int. Cl.
- *A61K 9/14* (2006.01)
- *A61K 47/00* (2006.01)
- *B65D 85/00* (2006.01)

(52) U.S. Cl.
USPC ........... 424/483; 424/489; 514/770; 514/777; 514/789; 206/459.5

(58) Field of Classification Search
USPC .................. 424/483, 489; 514/770, 777, 789; 206/459.5
See application file for complete search history.

(56) References Cited

U.S. PATENT DOCUMENTS

| | | | |
|---|---|---|---|
| 4,727,064 A | | 2/1988 | Pitha |
| 5,137,729 A | * | 8/1992 | Kuroya et al. ................ 424/435 |
| 7,067,116 B1 | * | 6/2006 | Bess et al. .................... 424/78.1 |
| 2001/0006677 A1 | * | 7/2001 | McGinity et al. ............. 424/449 |
| 2001/0022964 A1 | | 9/2001 | Leung et al. |
| 2004/0013731 A1 | * | 1/2004 | Chen et al. .................... 424/486 |
| 2004/0111275 A1 | * | 6/2004 | Kroll et al. ........................ 705/1 |
| 2005/0019588 A1 | | 1/2005 | Berry et al. |
| 2006/0083786 A1 | | 4/2006 | Chaudhari et al. |
| 2006/0264448 A1 | | 11/2006 | Pryde |
| 2006/0286108 A1 | | 12/2006 | Bell |

FOREIGN PATENT DOCUMENTS

EP 1267829 B1 5/2006

OTHER PUBLICATIONS

PCT International Search Report for International Application No. PCT/US2008/058877, dated Sep. 19, 2008, 3 pages.
Delsym product label approved by FDA Sep. 28, 2007, available at <www.fda.gov/cder/foi/label/2007/018658s022lbl.pdf>.
Nicorette product label approved by FDA Jun. 26, 2007, available at <www.fda.gov/cder/foi/label/2007/018612s049,02066s030lbl.pdf>.

* cited by examiner

*Primary Examiner* — Aradhana Sasan
(74) *Attorney, Agent, or Firm* — Hoffmann & Baron, LLP (57) ABSTRACT

The present invention relates to packaged orally consumable film dosage units for delivery of actives into the oral cavity. In particular, the packaged pharmaceutical product contains a complexate including a complexing agent and an active, an orally consumable film for delivery of the complexate and a package for containing the orally consumable film. The package includes indicia associated therewith. The indicia identifies the complexate as the active ingredient contained in the film, which is as a regulatory approvable chemical entity. The present invention also relates to methods of labeling, pricing, marketing and satisfying governmental regulations for such packaged pharmaceutical products.

21 Claims, 4 Drawing Sheets

PACKAGED FILM DOSAGE UNIT CONTAINING A COMPLEXATE

FIELD OF THE INVENTION

The present invention relates to packaged orally consumable film dosage units that dissolve in water. The orally consumable films may contain new active ingredients for delivery into the oral cavity. The new active ingredient contained in the film may be a complexate and the package may be labeled to indicate that such complexate is a regulatory approvable chemical entity.

BACKGROUND OF THE INVENTION

Orally consumable pharmaceutical products contain active ingredients for treatment of a wide variety of ailments. The packaging and labeling of such products are heavily regulated to protect the safety of consumers. Specifically, pharmaceutical products are labeled to provide the consumer with accurate information as to the contents of the product. Regulatory bodies worldwide oversee safety in pharmaceutical product labeling. In the United States, the Food and Drug Administration ("FDA") is responsible for regulating packaging and labeling of pharmaceutical products. Labeling for both prescription and over-the-counter ("OTC") drug products are regulated by the FDA. In particular, regulations require accurate identification of all active ingredients and their amounts contained in the pharmaceutical product. For instance, for OTC products, actives must be listed in hierarchical order of their relative amounts along with the concentration per unit dosage and pharmaceutical purpose of each.

To comply with such regulations, active ingredient information must be correctly identified on the product labeling. Actives that are complexed with another substance, such as a salt, form a new chemical entity having new and different functionality from the initial uncomplexed active. This new chemical entity is the active ingredient that can be used in a variety of different pharmaceutical products. There is a need to properly identify this new chemical entity as the active ingredient contained in such products. Therefore, accurate drug information can be provided to consumers and governmental regulations can be satisfied.

SUMMARY OF THE INVENTION

The present invention provides a new packaged film product which accurately provides information to a user regarding the active ingredient in the film product. The active ingredients are new chemical entities that have previously not been recognized as such.

In accordance with some embodiments of the present invention, there is provided a packaged pharmaceutical product including: a complexate including a complexing agent and an active; an orally consumable film for delivery of the complexate; and a package for containing the orally consumable film, the package including indicia associated therewith identifying the complexate as a regulatory approvable chemical entity.

In some embodiments, there is provided a method of labeling a packaged pharmaceutical product in a manner that is consistent with governmental drug regulations, including the steps of:
(a) providing a packaged pharmaceutical product containing:
  (i) a complexate including a complexing agent and a pharmaceutical active;
  (ii) an orally consumable film for delivery of the complexate; and
  (iii) a package for containing the orally consumable film; and
(b) adding indicia to the package, the indicia including a list of active ingredients contained in the orally consumable film and a list of inactive ingredients contained in the orally consumable film, where the complexate is listed as an active ingredient.

Some other embodiments provide a method of adjusting the sales price of a packaged orally consumable film product, which includes the steps of:
(a) selecting an orally consumable film product including a pharmaceutical active, the product having a manufacturing cost;
(b) selecting a complexing agent for use with the pharmaceutical active to form a complexate;
(c) estimating the cost of purchasing the complexing agent from a supplier;
(d) estimating the cost of manufacturing the complexate;
(e) determining the change in manufacturing cost of the orally consumable film product based on the additional cost estimates of steps (c) and (d); and
(f) adjusting the sales price of the product based on the change in manufacturing cost.

In some embodiments, there is provided a method of disseminating accurate drug information to consumers of a packaged pharmaceutical product, which includes the steps of:
(a) providing a packaged pharmaceutical product containing:
  (i) a complexate including a complexing agent and a pharmaceutical active;
  (ii) an orally consumable film for delivery of the complexate; and
  (iii) a package for containing the orally consumable film;
(b) providing indicia identifying the complexate as an active ingredient contained in the packaged pharmaceutical product; and
(c) exposing consumers to the indicia, thereby providing accurate information as to the active ingredient contained in the packaged pharmaceutical product.

Some embodiments provide a method of marketing an orally consumable film product containing a complexate as the active ingredient to consumers, which includes the steps of:
(a) identifying a first pharmaceutical product containing an active that has been marketed to consumers as an effective pharmaceutical product;
(b) providing a second pharmaceutical product including:
  (i) a complexate including a complexing agent and the active of step (a); and
  (ii) an orally consumable film for delivery of the complexate;
(c) educating consumers that the complexate contained in the second pharmaceutical product provides the same effectiveness as the active contained in the first pharmaceutical product; and
(d) marketing the second pharmaceutical product to consumers.

Some other embodiments provide a method of developing a sales price for a packaged orally consumable film product including a complexate as the active ingredient, which includes the steps of:

(a) selecting a pharmaceutical active and complexing agent to form the complexate included in the orally consumable film;
(b) estimating the cost of purchasing the complexing agent from a supplier;
(c) estimating the cost of purchasing the pharmaceutical active from a supplier;
(d) estimating the cost of manufacturing the complexate from the pharmaceutical active and the complexing agent;
(e) estimating the cost of producing and packaging the orally consumable film including the complexate;
(f) estimating the aggregate cost of safety and efficacy tests performed for the pharmaceutical active and the complexing agent individually;
(g) determining whether additional safety and efficacy tests for the complexate are required;
(h) estimating the cost associated with the additional safety and efficacy tests of step (g);
(i) adding the costs of the preceding steps to develop an estimated total manufacturing cost; and
(j) setting the sales price based on the estimated total manufacturing cost of the packaged orally consumable film product.

In some embodiments, there is provided a method of satisfying drug regulations promulgated by a regulatory body for an orally consumable film including a complexate as the active ingredient, the complexate including a complexing agent and a pharmaceutical active, which includes the steps of:
(a) submitting safety and efficacy test results for the complexing agent and safety and efficacy test results for the pharmaceutical active to the regulatory body;
(b) determining whether additional safety and efficacy tests for the complexate are required by the regulatory body;
(c) conducting the safety and efficacy tests of step (b); and
(d) submitting the results of the safety and efficacy tests of step (c) to the regulatory body to satisfy the drug regulations of the regulatory body for the orally consumable film product.

DETAILED DESCRIPTION OF THE INVENTION

The present invention relates to packaged pharmaceutical products that can be commercially marketed and sold to consumers. The packaged pharmaceutical products appropriately identify the active ingredient contained therein as an active that has obtained regulatory approval as a new chemical entity. More specifically, the packaged pharmaceutical products are orally consumable films, which rapidly dissolve in water. The orally consumable films include an active ingredient for delivery into the oral cavity. The active ingredient contained in the film is a complexate, which has new and different functionality over the initial uncomplexed active, as well as new clinical advantages.

A "complexate" is a chemical entity that is formed by a chemical complex, association or interaction between an active, such as a charged active, and a complexing agent, such as an acidic or basic resin. The resulting material formed from these two components is referred to herein as a "complexate". The complexate is a distinct chemical entity over the initial uncomplexed active. This chemical entity exhibits different functionality and offers new clinical advantages over the initial active. Furthermore, the complexate is a new chemical entity for purposes of FDA regulatory approval. For instance, if the complexate is considered a new chemical entity by the FDA, regulatory approval for use of the complexate as an active ingredient in orally consumable film products would be required by the FDA. The package of the orally consumable film is labeled to reflect that this complexate is one of the active ingredients contained in the product, rather than merely listing the initial uncomplexed active as the active ingredient. Therefore, the product packaging provides accurate disclosure information to consumers as to the active ingredient contained in the product.

The package containing the orally consumable film may be any conventional packaging material used for pharmaceutical products. For example, the package may be, without limitation, a pouch, box, cassette, blister pack, bag, or the like.

The package containing the film bears indicia thereon. The indicia provides information about the product ingredients to the consumer. In the pharmaceutical context, this information is extremely important to consumers who select products based on the active ingredients contained therein. Moreover, as discussed above, the listing of actives contained in pharmaceutical products is regulated by the FDA. The indicia on the package includes a list of active ingredients contained in the orally consumable film. The indicia identifies the complexate included in the orally consumable film as an active ingredient contained therein. Because the complexate is a regulatory approvable chemical entity for use in pharmaceutical products, it is appropriately identified as an active ingredient on the product indicia. Additional indicia also may include a list of inactive ingredients contained in the orally consumable film.

Figure 1:
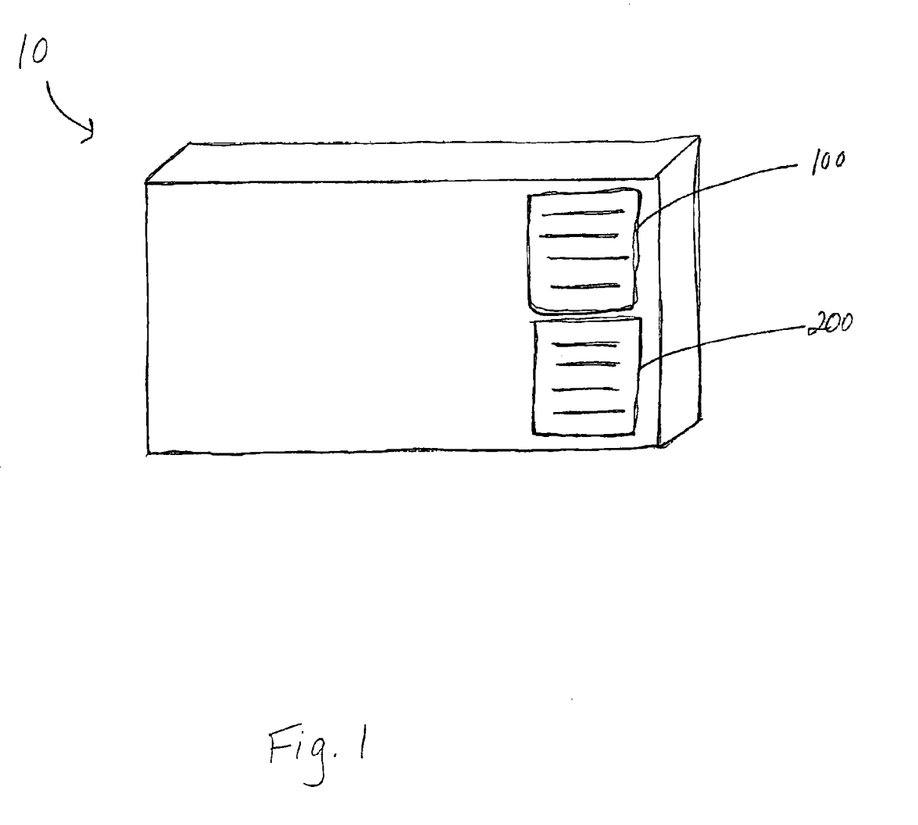
FIG. 1 is a side elevation view of a packaged pharmaceutical product in accordance with some embodiments of the present invention.

The indicia included on the packaged product may take a wide variation of forms, such as labels, symbols, bar codes, patterns and other means of communicating information. One preferred indicia is a label. The label or other indicia may be located on or affixed to any packaging component or the product per se. Any conventional means for affixing labels to a product package may be employed. For instance, as shown in FIG. 1, the packaged pharmaceutical product 10 may include multiple sets of indicia 100 and 200. The indicia of each set may be different. For example, the first indicia 100 may include a listing of active ingredients included in the orally consumable film contained in the package 10. The second indicia 200 may include a listing of inactive ingredients included in the orally consumable film contained in the package 10. The orally consumable film housed inside the package 10 includes a complexate. As mentioned above, the complexate is a chemical entity formed from a complexing agent and an active. Accordingly, the complexate itself is the active ingredient contained in the orally consumable film. The complexate as a chemical entity itself is listed in the indicia 100 as an active ingredient contained in the film. Therefore, the indicia appropriately conveys to the consumer that the complexate is one of the active ingredients contained in the orally consumable film.

Figure 2:
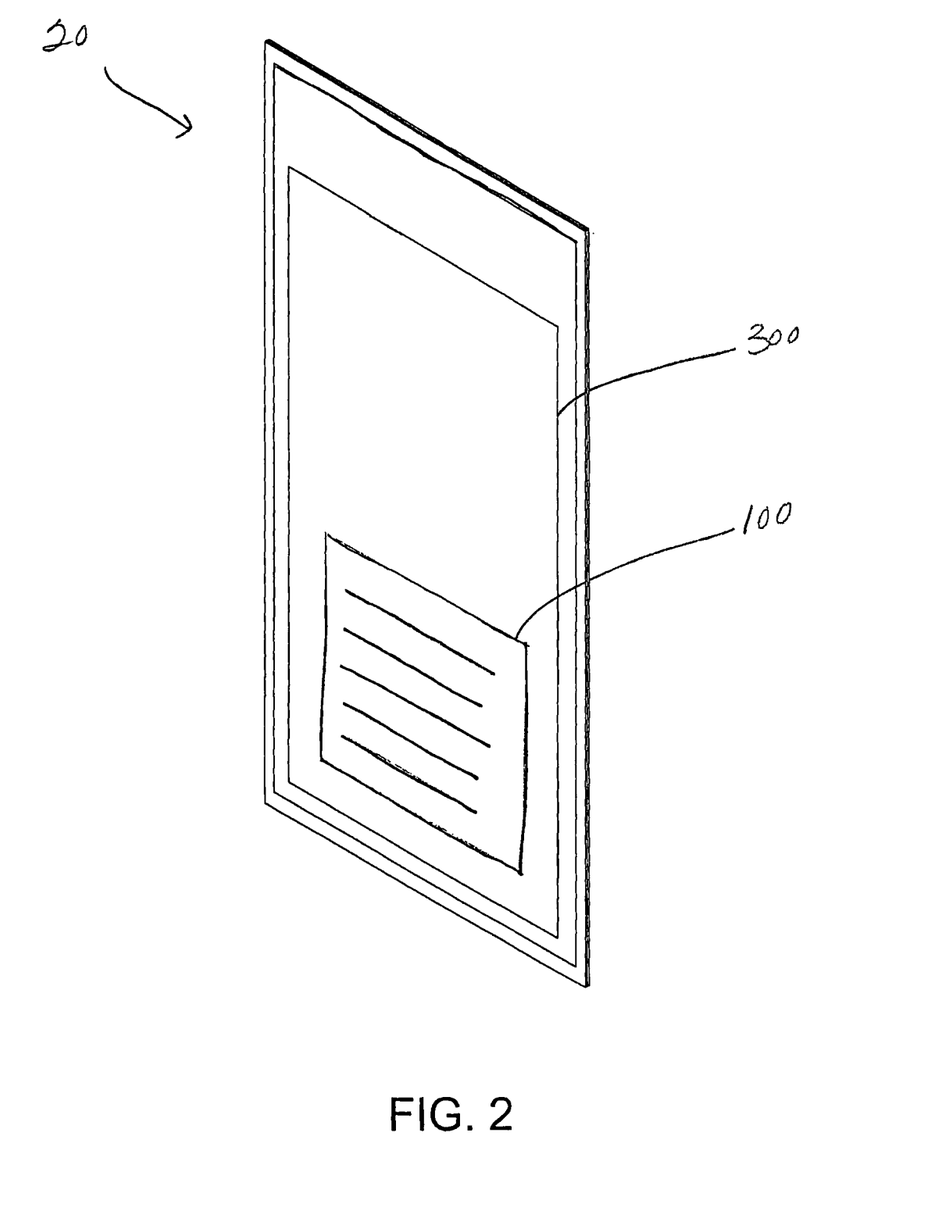
FIG. 2 is a side elevation view of a pouch containing an orally consumable film in accordance with some embodiments of the present invention.

In another embodiment shown in FIG. 2, for example, an orally consumable film 300 including a complexate is packaged in a pouch 20. The pouch 20 has top and bottom layers and may be sealed along the perimeter. The pouch may be sealed by heat sealing or with an adhesive, such as a pressure-sensitive adhesive. The top and bottom layers may be separated to allow for removal of the film 300 housed inside the pouch 20. The outside of the pouch, on the bottom and/or top layer, may include indicia 100 listing the active ingredients contained in the film. The complexate contained in the film is included in this listing of active ingredients. In such embodiments, therefore, film dosage units are packaged individually and each individual pouch provides the consumer with appropriate information as to the active ingredients contained in the film product.

Figure 3:
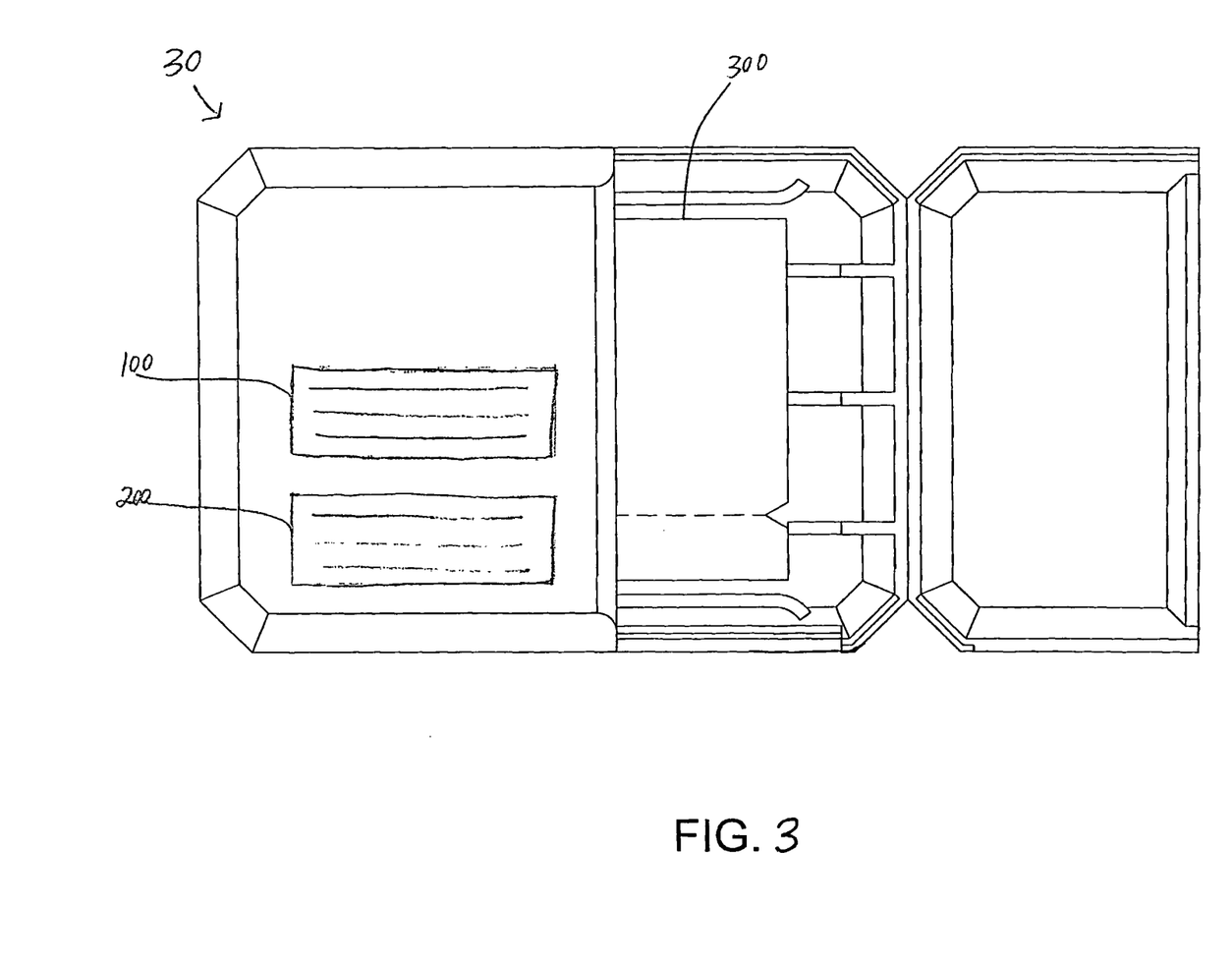
FIG. 3 is a topside view of a cassette containing a plurality of orally consumable films in accordance with some embodiments of the present invention.

In some other embodiments, a plurality of orally consumable films may be housed inside a cassette. For example, as shown in FIG. 3, a cassette 30 may contain a plurality of stacked orally consumable films 300. The films 300 include a complexate as an active ingredient. The cassette 30 may include two different sets of indicia 100 and 200 on the outer surface thereof. As described above, indicia 100 includes a listing of active ingredients included in the orally consumable films 300. Indicia 200 includes a listing of inactive ingredients included in the orally consumable films 300. The complexate included in the orally consumable films 300 is included in the list of active ingredients in indicia 100. The indicia 100 and 200 appropriately indicate to consumers the active and inactive ingredients contained in the product.

Figure 4:
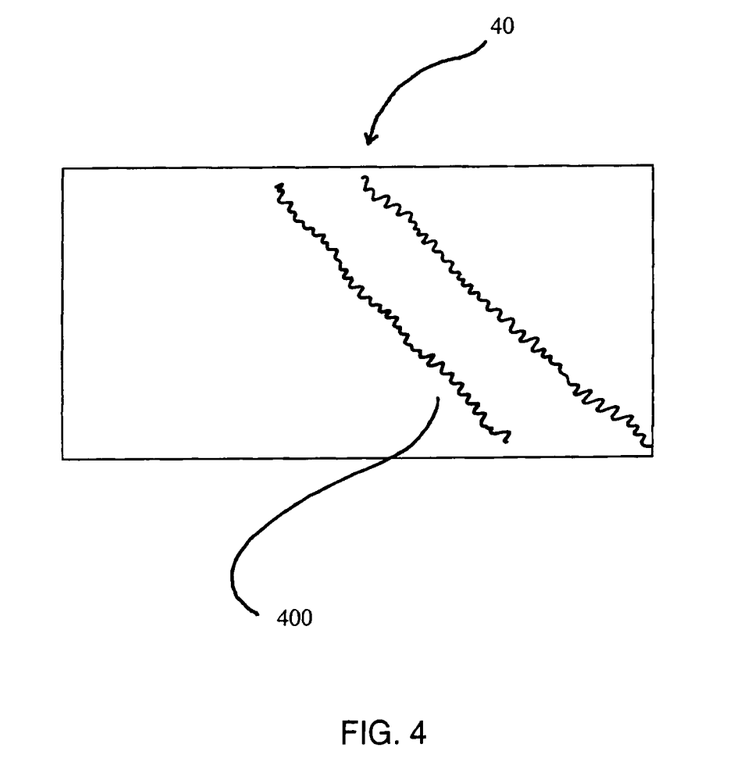
FIG. 4 is a topside view of an orally consumable film strip having indicia embossed or printed on its surface in accordance with some embodiments of the invention.

In another embodiment, the indicia indicating the complexate as an active ingredient may be positioned on the consumable film itself, such as by embossing, printing, stamping or other means. FIG. 4 shows a top view of an orally consumable film strip 40, with indicia 400 printed or embossed on its surface. The indicia includes identification of the complexate as the active ingredient.

It should be understood that any type of packaging may be used to house the orally consumable films and convey the information regarding the identification of the complexate as an active ingredient. Suitable orally consumable films and complexates for use in the packaged pharmaceutical products will be described in more detail below.

Orally Consumable Films

As described above, the packaged pharmaceutical products described herein include an orally consumable film for delivery of an active ingredient. The orally consumable films are fast-dissolving in the oral cavity and particularly suitable for delivery of actives. The active ingredient delivered by the films described herein is a complexate.

The films used in the packaged pharmaceutical products may be produced by a combination of at least one polymer and a polar solvent, optionally including other fillers known in the art. The solvent may be water, a polar organic solvent including, but not limited to, ethanol, isopropanol, acetone, methylene chloride, or any combination thereof. The film may be prepared by utilizing a selected casting or deposition method and a controlled drying process. Such processes are described in more detail in commonly assigned U.S. application Ser. No. 10/074,272, filed on Feb. 14, 2002, and published as U.S. Patent Publication No. 2003/0107149 A1, the contents of which are incorporated herein by reference in their entirety. Alternatively, the films may be extruded as described in commonly assigned U.S. application Ser. No. 10/856,176, filed on May 28, 2004, and published as U.S. Patent Publication No. 2005/0037055 A1, the contents of which are incorporated herein by reference in their entirety.

The polymer included in the films may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, polyethylene oxide, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. In some embodiments, films formed from such water soluble polymers may be sufficiently water soluble to be dissolvable upon contact with bodily fluids.

Other polymers useful for incorporation into the films include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers that provide mucoadhesive properties to the film, as well as a desired dissolution and/or disintegration rate. In particular, the time period for which it is desired to maintain the film in contact with the mucosal tissue depends on the type of active contained in the second delivery vehicle. Some actives may only require a few minutes for delivery through the mucosal tissue, whereas other actives may require up to several hours or even longer. Accordingly, in some embodiments, one or more water-soluble polymers, as described above, may be used to form the film. In other embodiments, however, it may be desirable to use combinations of water-soluble polymers and polymers that are water-swellable, water insoluble and/or biodegradable, as provided above. The inclusion of one or more polymers that are water-swellable, water insoluble and/or biodegradable may provide films with slower dissolution or disintegration rates than films formed from water-soluble polymers alone. As such, the film may adhere to the mucosal tissue for longer periods or time, such as up to several hours, which may be desirable for delivery of certain active components.

For instance, in some embodiments, the films may include polyethylene oxide alone or in combination with a second polymer component. The second polymer may be another water-soluble polymer, a water swellable polymer, a water insoluble polymer, a biodegradable polymer or any combination thereof. Suitable water-soluble polymers include, without limitation, any of those provided above. In some embodiments, the water-soluble polymer may include hydrophilic cellulosic polymers, such as hydroxypropyl cellulose and/or hydroxypropylmethyl cellulose. In accordance with some embodiments, polyethylene oxide may range from about 20% to 100% by weight in the polymer component, more specifically about 30% to about 70% by weight, and even more specifically about 40% to about 60% by weight. In some embodiments, one or more water-swellable, water insoluble and/or biodegradable polymers also may be included in the polyethylene oxide-based film. Any of the water-swellable, water insoluble or biodegradable polymers provided above may be employed. The second polymer component may be employed in amounts of about 0% to about 80% by weight in the polymer component, more specifically about 30% to about 70% by weight, and even more specifically about 40% to about 60% by weight.

The molecular weight of the polyethylene oxide also may be varied. In some embodiments, high molecular weight polyethylene oxide, such as about 4 million, may be desired to increase mucoadhesivity of the film. In some other embodiments, the molecular weight may range from about 100,000 to 900,000, more specifically from about 100,000 to 600,000, and even more specifically from about 100,000 to 300,000. In some embodiments, it may be desirable to combine high molecular weight (600,000 to 900,000) with low molecular weight (100,000 to 300,000) polyethylene oxide in the polymer component.

A variety of optional components and fillers also may be added to the films. These may include, without limitation: surfactants; plasticizers; polyalcohols; anti-foaming agents, such as silicone-containing compounds, which promote a smoother film surface by releasing oxygen from the film; thermo-setting gels such as pectin, carageenan, and gelatin, which help in maintaining the dispersion of components; inclusion compounds, such as cyclodextrins and caged molecules; coloring agents; and flavors. In some embodiments, an active component may be included in the film, in addition to the active component contained in the second delivery vehicle. Suitable active components for use in the film include any of those described below for use in the second delivery vehicle. The active contained in the film may be the same as or different from the active contained in the second delivery vehicle.

Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all film components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all film components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{1-8}$-, $C_{20}$- and $C_{22}$-fatty acids.

The total amounts used of the fats, mono-, di-glycerides and/or lecithins are up to about 5% and preferably within the range of about 0.5% to about 2% by weight of the total film composition.

It further may be useful to add silicon dioxide, calcium silicate, or titanium dioxide in a concentration of about 0.02% to about 1% by weight of the total composition. These compounds act as texturizing agents.

Lecithin is one surface active agent for use in the films described herein. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

Suitable coloring agents include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

Anti-foaming and/or de-foaming components may also be used with the films. These components aid in the removal of air, such as entrapped air, from the film-forming compositions. Such entrapped air may lead to non-uniform films. Simethicone is one particularly useful anti-foaming and/or de-foaming agent. The present invention, however, is not so limited and other anti-foam and/or de-foaming agents may suitable be used.

As a related matter, simethicone and related agents may be employed for densification purposes. More specifically, such agents may facilitate the removal of voids, air, moisture, and similar undesired components, thereby providing denser, and thus more uniform films. Agents or components which perform this function can be referred to as densification or densifying agents. As described above, entrapped air or undesired components may lead to non-uniform films.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Any other optional components described in commonly assigned U.S. application Ser. Nos. 10/074,272 and 10/856,176, referred to above, also may be included in the films described herein.

Complexates

In accordance with the present invention, the active ingredient included in the film is a complexate, which includes a complexing agent and an active. The complexate is a different chemical entity from the initial uncomplexed active. In some embodiments, for instance, the initial active is a charged active, which allows it to complex, interact or associate with an oppositely charged complexing agent, the formation of which is identifiable as a new active ingredient, i.e., a complexate.

The complexing agent may be any agent capable of chemically forming a complex, association or interaction with an active. For instance, the complexing agent may be an anionic complexing agent, which may react with an active having a cationic charge to form a complexate. Alternatively, the complexing agent may be a cationic complexing agent, which may react with an active having an anionic charge to form a complexate. In some embodiments, the complexing agent may be a multi-valent salt, which also may react with a charged active to form a complexate. In some embodiments, the complexing agent may be a zwitterion, which is a molecule carrying both a positive and a negative charge, and thus, can form a complex with a charged active. In some embodiments, the complexing agent may be an adsorbant or an absorbant material, such as, trimagnesium silicate or other absorbing silicates.

More specifically, in some embodiments, the complexing agent may be an ion exchange resin. Ion exchange resins may serve several different functions in pharmaceutical applications, including extended- or controlled-release, taste-masking, and improving the stability of actives. Ion exchange resins generally are insoluble macromolecules or polyelectrolytes that have electrically charged sites at which one ion may replace another ion. Cation-exchange resins have fixed electronegative charges that interact with counterions having the opposite, or positive, charge. Cation-exchange resins exchange positively charged cations. Anion-exchange resins have electropositive charges that interact with counterions having the opposite, or negative, charge. Anion-exchange resins exchange negatively charged anions.

In particular, an ion exchange resin for use herein may be a water-insoluble organic or inorganic matrix material having covalently bound functional groups that are ionic or capable of being ionized under appropriate conditions. The organic matrix may be synthetic (e.g., polymers or copolymers or acrylic acid, methacrylic acid, sulfonated styrene or sulfonated divinylbenzene) or partially synthetic (e.g., modified cellulose or dextrans). The inorganic matrix may be, for example, silica gel modified by the addition of ionic groups. Most ion exchange resins are cross-linked by a crosslinking agent, such as divinylbenzene.

Ion exchange resins for use herein may be categorized into four main types depending on their functional groups: strongly acidic (e.g., sulfonic acid groups); strongly basic (e.g., trimethylammonium groups); weakly acidic (e.g., carboxylic acid groups); and weakly basic (e.g., amino groups).

In some embodiments, for instance, an acidic resin may be employed. The acidic resin may be combined with a basic drug to form a complexate. Examples of acidic resins that can be combined with basic drugs include, but are not limited to, partially neutralized poly(acrylic acid), crosslinked acrylic acid copolymers (such as Indion 414), sodium polystyrene sulfonate (such as Amberlite IRP-69), copolymers of methy-acrylic acid crosslinked with divinylbenzene (such as Amberlite IRP-64), and polacrilin potassium.

Examples of basic drugs that can be combined with any of the acidic resins set forth above include, but are not limited to, levobetaxolol hyrdrochloride, roxithromycin, dicyclomine hydrochloride, montelukast sodium, dextromethorphan hydrobromide, diphenhydramine hydrochloride, orbifloxacin, ciprofloxacin, enoxacin, grepafloxacin, levofloxacin, lomefloxacin, nalidixic acid, acycloguanosine, timidazole, deferiprone, cimetidine, oxycodone, remacemide, nicotine, morphine, hydrocodone, rivastigmine, propanolol, betaxolol, chlorpheniramine, and paroxetine.

In some embodiments, a basic resin may be employed. The basic resin may be combined with an acidic drug to form a complexate. Examples of basic resins that can be used to form complexates include, but are not limited to, polyvinylpyrrolidone, polylysine, polyarginine, and polyhistidine.

Examples of acidic drugs that can be combined with any of the basic resins set forth above include, but are not limited to, nicotinic acid, mefanamic acid, indomethacin, diclofenac, repaglinide, ketoprofen, ibuprofen, valproic acid, lansoprazole, ambroxol, omeprazole, acetaminophen, topiramate, amphotericin B, and carbemazepime.

In some other embodiments, the complexing agent may rely on weak bonding forces, such as Van der Waals forces or hydrogen bonding, to form a complexate with an initial active. Such complexing agents may include caged molecules, such as cyclodextrins. Cyclodextrins generally are cyclic oligosaccharides composed of alpha-D-glucopyranose units. Common cyclodextrins include alpha-, beta- and gamma-cyclodextrins, which contain 6, 7 and 8 glucose units, respectively. Cyclodextrins have a toroidal shape with a generally hydrophobic interior cavity and a generally hydrophilic exterior, which imparts water-solubility to the molecule. This characteristic allows cyclodextrins to form inclusion complexes, i.e., host-guest complexes, with hydrophobic molecules to increase the water-solubility thereof. More specifically, guest molecules interact with the interior cavity of the cyclodextrin to become entrapped and form a stable association therewith. Due to the hydrophilic exterior of the cyclodextrin, the inclusion complex is water-soluble, thereby increasing the release of poorly soluble drugs complexed therewith.

Examples of such complexing agents include, but are not limited to, alpha-cyclodextrin, beta-cyclodextrin, gamma-cyclodextrin and derivatives of cyclodextrins, such as hydroxyalkylated cyclodextrins. Examples of drugs that can be combined with this type of complexing agent are many and are determined by the fit of the drug within the complexing agent, e.g., cyclodextrin. For example, anthracyclines form good complexes with gamma-cyclodextrin. Complexes of other cyclodextrins are described in U.S. Pat. No. 4,727,064, which is incorporated herein by reference in its entirety.

In some embodiments described herein, the complexing agent may be a zeolite. Zeolites are minerals having a microporous structure. Zeolites include naturally occurring minerals and synthetic compounds, which generally are characterized by an alumino-silicate framework with an open structure that can accommodate cations, such as $Na^+$, $K^+$, $Ca^{2+}$, $Sr^{2+}$ and $Ba^{2+}$. The cations reside in cavities in the crystal structure and can be readily exchanged for others in a solution. Zeolites can be of various different types, such as P-type and X-type, and with numerous counterions, such as sodium and calcium. Additionally, zeolites can be used in combination with ammonium salts, such as hexadecyltrimethyl ammonium bromide. An example of this is a complex of chloroquin with a P-type zeolite with a sodium counterion and in the presence of dodecyltrimethylammonium bromide.

In some embodiments, the complexing agent may rely on any type of molecular entanglement, as such entanglement is understood in quantum theory. Any materials that are bound in any way are by definition "entangled" in quantum theory.

In such embodiments, the molecular chains of a complexing agent, such as a polymer, are sufficiently entangled to trap or bind the active, thereby forming the complexate. In instances when the molecular weight is excessive, the ability of the thus formed complexate to release the active may be hampered or too slow for practical purposes. Thus, the upper limit for molecular weight of the complexing agent is that which still provides efficacy for its intended use. The upper limits of molecular weight will of course depend on the polymer chosen, as well as the active, since the behavior of the complexate is dependent to a large degree on its formative components.

In some embodiments, the complexing agent may promote volatilization.

In addition to the drugs specifically provided above, any of a variety of pharmaceutical actives, medicaments and bioactive active substances may be used in forming the complexates. The following is a non-exhaustive list of exemplary actives.

A wide variety of medicaments, bioactive active substances and pharmaceutical actives may be employed. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs for other preferred active ingredients for use in the present invention include anti-diarrheals such as immodium AD, anti-histamines, anti-tussives, decongestants, vitamins, and breath fresheners. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and $Ca^H$-antagonists such as nifedipine (available as Procardia® and Adalat®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafils, such as Viagra®, tadalafils, such as Cialis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

An anti-oxidant may also be added to the film to prevent the degradation of an active, especially where the active is photosensitive.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

In addition, in some embodiments, the complexate may be taste-masked prior to incorporation into the orally consumable film. A detailed description of suitable taste-masking agents and processes for taste-mask coating is set forth in International Application No. PCT/US02/32594, entitled "Uniform Films For Rapid Dissolve Dosage Form Incorporating Taste-Masking Compositions," filed Oct. 11, 2002, and which published as WO 2003/030883 (claiming priority to U.S. Provisional Application No. 60/414,276 of the same title, filed Sep. 27, 2002), the contents both of which are incorporated by reference herein in their entirety.

In any of the embodiments described above, the active may be present in amounts of about 0.01% to about 60% by weight of the complexate. The complexing agent may be present in amounts of about 0.2% to about 20% by weight of the complexate. The complexing agents described above may have molecular weights of about 2,000 or more.

Methods of Labeling, Pricing, Marketing and Satisfying Regulations for Complexates The present invention also is directed to methods of labeling a packaged pharmaceutical product in a manner that is consistent with governmental drug regulations. More specifically, the FDA regulates the packaging requirements for pharmaceutical products in the United States. Product packaging must include a listing of the active ingredients contained in the product. Inactive ingredients are listed separately. In accordance with some embodiments described herein, a packaged pharmaceutical product is provided. The packaged pharmaceutical product includes a complexate, as described above, an orally consumable film for delivery of the complexate and a package for containing the orally consumable film. Indicia are added to the package, which include a list of active ingredients contained in the orally consumable film and a list of inactive ingredients contained in the orally consumable film. The complexate is included in the list of active ingredients on the product package. In particular, as discussed above, the complexate is the active ingredient itself due to its interaction with an initial active. Once the complexing agent interacts with the active to form the complexate, the initial active no longer exists. Therefore, listing the initial active on the product packaging would not be consistent with FDA regulations. Rather, the active ingredient contained in the film is the complexate. Therefore, including the complexate in the list of active ingredients on the indicia is consistent with FDA regulations. Moreover, listing the complexate as such appropriately informs consumers as to the active ingredient contained in the product.

The present invention also provides methods of adjusting the sales price of a packaged orally consumable film product. In accordance with such methods, an orally consumable film product, which includes a pharmaceutical active, is selected. The manufacturing cost of the orally consumable film product is known. A complexing agent then is selected for use with the pharmaceutical active. Once the particular complexing agent is selected, the cost of purchasing the complexing agent from a supplier is estimated. Additionally, the cost of manufacturing the complexate from the selected complexing agent and the pharmaceutical active is estimated. Subsequently, a determination is made as to the change in manufacturing cost of the orally consumable film product based on these additional cost estimates. Based on this change in manufacturing cost, the sales price of the product may be adjusted. For instance, the cost of purchasing the complexing agent may add a substantial increase to the cost of manufacturing the product. As such, the sales price per unit of the product may be adjusted upwardly to account for the increased cost.

The sales price of the film product also may be adjusted to compensate for various other costs. For instance, the modification of the product to include a complexate rather than the original active may require additional safety and efficacy tests. There are costs associated with conducting such clinical tests, as well as submitting the results of the tests to the requisite regulatory body for approval. The modification of the product to include a complexate also may require a labeling change on the product packaging. The development and production of new packaging also involves increased costs. The sales price per unit of the product may be adjusted based on these additional costs, as well.

Finally, a determination may be made as to whether or not the adjusted sales price of the product is viable in the consumer marketplace. If the adjusted sales price is not viable, all of the manufacturing costs may need to be reexamined to determine where costs can be reduced.

Some embodiments of the present invention are directed to methods of developing a sales price for a packaged orally consumable film product including a complexate as the active ingredient. A pharmaceutical active and complexing agent are selected for forming the complexate to be included in the orally consumable film. The cost of purchasing the complexing agent from a supplier is estimated, as well as the cost of purchasing the pharmaceutical active from a supplier. The cost of manufacturing the complexate from the pharmaceutical active and the complexing agent also is estimated, as well as the cost of producing and packaging the orally consumable film including the complexate. The aggregate cost of safety and efficacy tests performed for the pharmaceutical active and the complexing agent individually is estimated. Then, a determination is made as to whether or not additional safety and efficacy tests for the complexate are required. Additional safety and efficacy tests may be required by a regulatory body, e.g., the FDA, to satisfy governmental drug regulations. If such additional tests are required, the costs associated with conducting such tests and submitting the results to the regulatory body are estimated. Finally, all of the cost estimates are added together to develop an estimated total manufacturing cost for the product and then the sales price may be set based on this estimated total manufacturing cost.

The present invention additionally is directed to methods of disseminating accurate drug information to consumers of a packaged pharmaceutical product. It is important to provide accurate information to consumers of pharmaceutical products such that they can make informed decisions as to whether or not to purchase or consume a particular product. For instance, some consumers may have allergic reactions to certain pharmaceutical actives, and thus, cannot consume products containing such actives. In accordance with the methods provided herein, a packaged pharmaceutical product is provided. The product includes a complexate, as described above, an orally consumable film for delivery of the complexate and a package for containing the orally consumable film. Indicia identifying the complexate as an active ingredient contained in the packaged pharmaceutical product is provided. The indicia may be directly associated with the packaged pharmaceutical product. For example, the indicia may be a label on the product or an insert inside the product packaging. In addition, as an alternative to the presence of indicia on the package, indicia may also be placed on the consumable film per se. In some other embodiments, the indicia may be indirectly associated with the product, such as a print, television or internet advertisement, or a product brochure at a physician's office. Consumers are exposed to the indicia, by reading the product packaging, viewing the advertisement, or the like, thereby providing accurate information as to the active ingredient contained in the packaged pharmaceutical product.

In some embodiments, the present invention also provides methods of marketing an orally consumable film product containing a complexate as the active ingredient. In accordance therewith, a first pharmaceutical product is identified. This product contains an active that has been marketed to consumers as an effective pharmaceutical active. A second pharmaceutical product is provided, which includes a complexate formed from a complexing agent and the same active contained in the first pharmaceutical product. The product also includes an orally consumable film for delivery of the complexate. Consumers are educated that the complexate contained in the second pharmaceutical product provides the same effectiveness as the active contained in the first pharmaceutical product. Such education may be effected via advertisements, such as print, television and internet advertisements. Educational product information also may be supplied to physicians to disseminate to their patients. The second pharmaceutical product then may be marketed to consumers on this basis.

The present invention additionally is directed to methods of satisfying drug regulations promulgated by a regulatory body for an orally consumable film including a complexate as an active ingredient. In accordance with such methods, safety and efficacy test results for the complexing agent and safety and efficacy test results for the pharmaceutical active are submitted to the regulatory body, such as the FDA. A determination then is made as to whether or not additional safety and efficacy tests for the complexate are required by the regulatory body. If such additional tests are required to satisfy the regulations, these tests are conducted and the results are submitted to the regulatory body to satisfy the drug regulations for the orally consumable film product. Additionally, a determination may be made as to whether or not a change in labeling on the package of the film product is required to satisfy drug regulations. In particular, the labeling may need to be changed to appropriately identify the complexate as an active ingredient contained in the product. If necessary, the product labeling also may be changed to satisfy the governmental drug regulations.

EXAMPLES

Example 1

Packaged pharmaceutical products of the present invention including orally consumable films for delivery of a complexate are prepared.

First, the complexate was prepared by placing 16.24 g of highly purified crosslinked polystyrene copolymer in sodium form (commercially available under the trade name Tulsion 344 from Thermax), which is the complexing agent, in an 8 ounce screw cap bottle with 125 ml of distilled water and stirring with a magnetic stirrer for 5 minutes. 5.41 g of loperamide HCl, which is the initial active, was added to the bottle and stirred with a magnetic stirrer for 16 hours with a screw cap on the bottle. The ratio of crosslinked polystyrene copolymer to loperamide HCl was 3:1. The reaction mixture was filtered through a Buchner funnel to separate the solid material from the liquid. The solid material was washed on the filter with distilled water. The filtrate was saved. The solid material collected on the filter was allowed to air dry.

The solid material then was dried in a 95° C. air oven in an aluminum foil dish for 2.5 hours to achieve a constant weight of dried material. 20.964 g of dried material was recovered. The dried solid material, which is the complexate, was sieved through a 60 mesh screen and stored in a screw cap bottle.

The orally consumable films incorporating the complexate were prepared using the components listed in Table 1.

TABLE 1

| Component | Amount in g (wt %) |
| --- | --- |
| Hydroxyproplymethyl cellulose | 4.88 g (34.87%) |
| Polyethylene Oxide | 2.44 g (17.435%) |
| Polydextrose | 2.44 g (17.435%) |
| Sucralose | 0.63 g (4.5%) |
| Flavor enhancer[1] | 0.07 g (0.5%) |
| Menthol | 0.14 g (1%) |
| Blue color (FD&C Blue #1) | 0.004 g (0.03%) |
| Titanium Dioxide | 0.14 g (1%) |
| Distilled Water | 36 g |

[1]Magna Sweet 100, available from Mafco Worldwide Corp.

To prepare the orally consumable films, first the menthol, blue color, titanium dioxide and distilled water were added to a Degussa 1100 bowl. A blend of the hydroxypropylmethyl cellulose, polyethylene oxide, polydextrose, sucralose and flavor enhancer was prepared and added to the bowl. The mixture was stirred for 20 minutes (at 125 rpm, 60% vacuum) using a Degussa Multivac Compact apparatus. The mixture then was stirred for 20 minutes (at 125 rpm, 90% vacuum), 12 minutes (at 125 rpm, 98% vacuum) and 8 minutes (at 125 rpm, 100% vacuum) to form a masterbatch.

In a first batch of orally consumable films, 18.698 g of the masterbatch containing 4.298 g solids was added to a small fabricated glass bowl. A solution of 0.006 g (0.1 wt %) butylated hydroxytoluene (BHT), 0.06 g (1 wt %) cooling agent, 0.17 g (3 wt %) menthol and 0.28 g (5 wt %) raspberry flavor was added to the bowl. The solution was prepared using the Degussa Multivac Compact apparatus by stirring for 4 minutes (at 125 rpm, 100% vacuum). 0.79 g (14.13 wt %) of the complexate, as prepared above, was added. The solution was stirred for 4 minutes (at 100 rpm, 100% vacuum). The solution was cast into film using a K-control coater with the micrometer adjustable wedge bar set at 335 microns. The film was dried for 13 minutes in an 80° C. air oven. The final film had a moisture content of 4.84%. The film was cut into 1¼ by 1 inch strips which each weighed 50 mg.

In a second batch of orally consumable films, 18.698 g of the masterbatch containing 4.298 g solids was added to a small fabricated glass bowl. A solution of 0.006 g (0.1 wt %) butylated hydroxytoluene (BHT), 0.06 g (1 wt %) cooling agent and 0.45 g (8 wt %) peppermint flavor was added to the bowl. The solution was prepared using the Degussa Multivac Compact apparatus by stirring for 4 minutes (at 125 rpm, 100% vacuum). 0.79 g (14.13 wt %) of the complexate, as prepared above, was added. The solution was stirred for 4 minutes (at 100 rpm, 100% vacuum). The solution was cast into film an dried as described for the first batch above. The final film had a moisture content of 2.94%. The film was cut into 1¼ by 1 inch strips which each weighed 51-57 mg.

The orally consumable films prepared in the first and second batches above include a complexate and can be packaged in accordance with the present invention. For example, the orally consumable films are individually packaged in pouches. Each pouch has top and bottom layers. Once the orally consumable film is positioned therein, the top and bottom layers of the pouch are sealed along the perimeter by heat sealing. The outside of the pouch, on the bottom and/or top layer, includes indicia listing the active ingredients contained in the orally consumable film housed therein. The complexate contained in the film is included in this listing of active ingredients. The complexate itself is listed as a chemical entity in this listing of active ingredients, rather than the initial active, loperamide. Therefore, each individual pouch provides the consumer with appropriate information as to the active ingredients contained in the orally consumable film.

Example 2

Packaged pharmaceutical products of the present invention including orally consumable films for delivery of a complexate are prepared.

First, the complexate was prepared by placing 4 g of highly purified crosslinked polystyrene copolymer in sodium form (commercially available under the trade name Tulsion 344), which is the complexing agent, in a 50 ml beaker with 16 g of distilled water and stirring with a magnetic stirrer for 5 minutes. 2 g of dextromethorphan hydrobromide, which is the initial active, was added to the beaker and allowed to stir with the magnetic stirrer for about 3 hours and 45 minutes. The reaction mixture was allowed to settle and the water portion was decanted. Additional water was added to the beaker and allowed to settle. The water portion was again removed by decanting. The solid reaction product, which is the complexate, was dried for 15 hours in a 30° C. air oven.

The orally consumable films incorporating the complexate were prepared using the components listed in Table 2.

TABLE 2

| Component | Amount in g (wt %) (unless indicated otherwise) |
|---|---|
| Hydroxypropylmethyl cellulose | 1.76 g (23.9%) |
| Hydroxypropyl cellulose | 0.59 g (7.97%) |
| Sucralose | 0.18 g (2.5%) |
| Flavor enhancer[1] | 0.04 g (0.5%) |
| Complexate | 4.15 g (56.23%) |
| Flavor enhancer[2] | 0.05 g (0.65%) |
| Masking Agent | 0.04 g (0.5%) |
| Bubblegum flavor | 0.37 g (5%) |
| Peppermint flavor | 0.18 g (2.5%) |
| Polydimethylsiloxane Emulsion | 0.02 g (0.25%) |
| Distilled Water | 13.71 g |
| Red Food Coloring | 3 drops |

[1]Magna Sweet 100, available from Mafco Worldwide Corp.
[2]Prosweet Flavor N&A K, available from Virginia Dare To prepare the orally consumable films, first the polydimethylsiloxane emulsion, distilled water and red food coloring were added to a Degussa 1100 bowl equipped with an addition port. Then the mixture was stirred for 4 minutes (at 100 rpm, 0% vacuum) using a Degussa Multivac Compact apparatus. A blend of the hydroxypropylmethyl cellulose, hydroxypropyl cellulose, sucralose and the first flavor enhancer was added to the mixture. The mixture was stirred for 20 minutes (at 100 rpm, 0% vacuum), 4 minutes (at 100 rpm, 90% vacuum), 4 minutes (at 100 rpm, 100% vacuum) and then 4 minutes (at 100 rpm, 100% vacuum). The complexate, prepared as described above, was added. The mixture then was stirred for 4 minutes (at 100 rpm, 30% vacuum). 3.51 g of water was added to yield 30% solids and the second flavor enhancer, masking agent, bubblegum flavor and peppermint flavor were added.

The solution was cast into film using a K-control coater with the a 350 micron smooth bar onto release paper. The film was dried for 8 minutes in a 90° C. air oven. The final film had a moisture content of 7.02%.

The film prepared above can be divided into individual orally consumable film dosage units. The orally consumable films include a complexate and can be packaged in accordance with the present invention. For example, the orally consumable films can be packaged into pouches, as described in Example 1. Alternatively, a plurality of the orally consumable films can be packaged into a cassette. More specifically, the orally consumable films are stacked inside a cassette. Indicia are located on the outer surface of the cassette, which includes a listing of active ingredients included in the orally consumable films housed therein. The complexate itself is listed as a chemical entity in this listing of active ingredients, rather than the initial active, dextromethorphan. Therefore, the package appropriately indicates to consumers the active ingredients contained in the product.

Example 3

Packaged pharmaceutical products of the present invention including orally consumable films for delivery of a complexate are prepared.

First, the complexate was prepared by placing 13.5 g of highly purified crosslinked polystyrene copolymer in sodium form (commercially available under the trade name Tulsion 344), which is the complexing agent, in an 8 ounce screw cap bottle with 100 ml of distilled water and stirring with a magnetic stirrer for 5 minutes. 5.4 g of cetirizine dihydrochloride (commercially available as Zyrtec from Pfizer), which is the initial active, was added to the bottle and allowed to stir with the magnetic stirrer for 16 hours with a screw cap on the bottle. The ratio of the highly purified crosslinked polystyrene copolymer to cetirizine dihydrochloride was 2.5 to 1. The reaction mixture was filtered through a Buchner funnel to separate the solid material from the liquid. The solid material was washed on the filter with distilled water. The filtrate was saved.

The solid material collected on the filter was dried in a 95° C. air oven in an aluminum foil dish for 2 hours to achieve a constant weight of dried material. 17.06 g of dried material was recovered. The dried solid material, which is the complexate, was sieved through a 60 mesh screen and stored in a screw cap bottle.

The orally consumable films incorporating the complexate were prepared using the components listed in Table 3.

TABLE 3

| Component | Amount in g (wt %) |
|---|---|
| Polyethylene Oxide | 2.4 g (30%) |
| Corn Starch | 0.8 g (10%) |
| Polydextrose | 0.8 g (10%) |
| Sucralose | 0.32 g (4%) |
| Flavor enhancer[1] | 0.04 g (0.5%) |
| Complexate | 2.55 g (31.82%) |
| Butylated Hydroxytoluene (BHT) | 0.008 g (0.1%) |
| Cooling agent | 0.08 g (1%) |
| Juicy fruit flavor | 0.092 g (1.15%) |
| Grape flavor | 0.83 g (10.35%) |
| Menthol | 0.08 g (1%) |
| Red color (FD&C Red #40) | 0.003 g (0.04%) |
| Blue color (FD&C Blue #1) | 0.003 g (0.04%) |
| Distilled Water | 12 g |

[1]Magna Sweet 100, available from Mafco Worldwide Corp.

To prepare the orally consumable films, the menthol, red and blue colors and water were added to a small fabricated glass bowl. The a mixture of polyethylene oxide, corn starch, polydextrose, sucralose and the flavor enhancer was added to the bowl. The solution was prepared using a Degussa Multivac Compact apparatus by stirring for 20 minutes (at 100 rpm, 60% vacuum), 20 minutes (at 100 rpm, 90% vacuum), 12 minutes (at 100 rpm, 98% vacuum) and then 8 minutes (at 100 rpm, 100% vacuum). Water was added to the solution to make up for water loss. Then the solution was stirred for 4 minutes (at 100 rpm, 100% vacuum). A solution of BHT, cooling agent, juicy fruit and grape flavors was added and then stirred for an 4 additional minutes (at 100 rpm, 100% vacuum). The complexate then was added to the solution.

The solution was cast into film using a K-control coater with the micrometer adjustable wedge bar set at 500 microns. The film was dried for 14 minutes in an 80° C. air oven. The final film had a moisture content of 2.49%. The film was cut into 1¼ by 1 inch strips which each weighed 110 mg.

These orally consumable film strips include a complexate and can be packaged in accordance with the present invention. For example, the orally consumable films can be packaged into pouches, as described in Example 1, or a plurality of the films can be stacked in a cassette, as described in Example 2. Indicia are located on the outer surface of the pouch or cassette, which lists the complexate as an active ingredient included in the films contained in the package, thereby appropriately indicating to consumers the active ingredients contained in the product.

Example 4

Packaged pharmaceutical products of the present invention including orally consumable films for delivery of a complexate are prepared.

First, the complexate is prepared including the components listed in Table 4.

TABLE 4

| Component | Amount (g) |
|---|---|
| Naproxen | 2.5 g |
| Cyclodextrin[1] | 10.0 g |
| Water | 100 g |

[1]Cavamax W7, available from Wacker Chemie AG

The naproxen and cyclodextrin are added to water and stirred with a magnetic stirrer for 4 hours at 60° C. The solution is then evaporated using a rotary distillation unit under vacuum. The remaining powder is then dried to a constant weight using a mechanical oven at 80° C. to form the complexate.

The orally consumable films incorporating the complexate are prepared using the components listed in Table 5.

TABLE 5

| Component | Amount in g (wt %) |
|---|---|
| Hydroxypropylmethyl cellulose | 0.95 g (29.62%) |
| Polyethylene oxide | 0.47 g (14.8%) |
| Polydextrose | 0.47 g (14.8%) |
| Sucralose | 0.06 g (2%) |
| Flavor enhancer[1] | 0.02 g (0.5%) |
| Menthol | 0.03 g (1%) |
| Blue color (blue #1) | 0.001 g (0.030%) |
| Titanium dioxide | 0.03 g (1%) |
| Complexate | 1 g (31.25%) |
| Raspberry Flavor | 0.16 g (5%) |

[1]Magna Sweet 100, available from Mafco Worldwide Corp.

To prepare the orally consumable films, 7.5 g of water is heated to 80° C. in a Degussa bowl. Hydroxypropylmethyl cellulose, polyethylene oxide, polydextrose, sucralose, flavor enhancer, menthol, blue color and titanium dioxide are added to the bowl and stirred for 2 hours using a Degussa Multivac Compact apparatus. The temperature is allowed to cool over the 2 hour period. 1 hour of the mixing is at room temperature. Vacuum is gradually added with mixing over 30 minutes until all air is removed. The raspberry flavor is added and vacuum again added (28 inches Hg) for 12 minutes. The complexate then is added and vacuum (28 inches Hg) with stirring to remove any air. The solution/suspension is coated using a K-control coater with a micrometer setting of 530 microns onto release paper. The film is dried for 8 minutes at 80° C. in an air oven. The film is cut into 1 inch by 1¼ inch strips, which weigh 80 mg.

These individual orally consumable film strips include a complexate and can be packaged in accordance with the present invention. For example, the orally consumable films can be packaged into pouches, as described in Example 1, or a plurality of the films can be stacked in a cassette, as described in Example 2. Indicia are located on the outer surface of the pouch or cassette, which lists the complexate as an active ingredient included in the films contained in the package, thereby appropriately indicating to consumers the active ingredients contained in the product.

What is claimed is:

1. A packaged pharmaceutical product comprising:
a taste-masked complexate comprising a complexing agent comprising an ion exchange resin and an active, wherein said ion exchange resin controls the release of said active and improves the stability of said active and wherein said complexate is a distinct chemical entity when compared to said active;
an orally consumable film comprising said complexate, wherein the orally consumable film has mucoadhesive properties and a minimum dissolution time of at least a few minutes; and
a package for containing said orally consumable film, said package comprising indicia associated therewith identifying said complexate as a regulatory approvable chemical entity.

2. The pharmaceutical product of claim 1, wherein said active comprises a charged active.

3. The pharmaceutical product of claim 1, wherein said complexing agent comprises an anionic complexing agent.

4. The pharmaceutical product of claim 1, wherein said complexing agent comprises a cationic complexing agent.

5. The pharmaceutical product of claim 2, wherein said charged active comprises an anionic active.

6. The pharmaceutical product of claim 2, wherein said charged active comprises a cationic active.

7. The pharmaceutical product of claim 1, wherein said complexing agent comprises a multi-valent salt.

8. The pharmaceutical product of claim 1, wherein said complexing agent comprises a zeolite.

9. The pharmaceutical product of claim 1, wherein said complexing agent comprises a caged molecule.

10. The pharmaceutical product of claim 9, wherein said caged molecule comprises a cyclodextrin.

11. The pharmaceutical product of claim 1, wherein said package comprises a pouch.

12. The pharmaceutical product of claim 1, wherein said package comprises a box.

13. The pharmaceutical product of claim 1, wherein said package comprises a cassette.

14. The pharmaceutical product of claim 1, wherein said indicia comprises a label.

15. The pharmaceutical product of claim 14, wherein said label is located on said package.

16. The pharmaceutical product of claim 14, wherein said label is affixed to said package.

17. The pharmaceutical product of claim 1, wherein said indicia comprises a list of active ingredients.

18. The pharmaceutical product of claim 1, wherein said indicia identifies said complexate as an active ingredient.

19. A method of labeling a packaged pharmaceutical product in a manner that is consistent with governmental drug regulations, comprising the steps of:
(a) providing a packaged pharmaceutical product comprising:
 (i) a taste-masked complexate comprising a complexing agent comprising an ion exchange resin and a pharmaceutical active, wherein said ion exchange resin controls the release of said active and improves the stability of said active and wherein said complexate is a distinct chemical entity when compared to said active;
 (ii) an orally consumable film comprising said complexate, wherein said orally consumable film has mucoadhesive properties and a minimum dissolution time of at least a few minutes; and
 (iii) a package for containing said orally consumable film;
(b) adding indicia to said package, said indicia comprising a list of active ingredients contained in said orally consumable film and a list of inactive ingredients contained in said orally consumable film, wherein said complexate is listed as an active ingredient.

20. The method of claim 19, wherein said indicia added to said package in step (b) identifies said complexate as a regulatory approvable chemical entity.

21. A method of disseminating accurate drug information to consumers of a packaged pharmaceutical product, comprising the steps of:
(a) providing a packaged pharmaceutical product comprising:
 (i) a taste-masked complexate comprising a complexing agent comprising an ion exchange resin and a pharmaceutical active wherein said ion exchange resin controls the release of said active and improves the stability of said active and wherein said complexate is a distinct chemical entity when compared to said active;
 (ii) an orally consumable film comprising said complexate, wherein said orally consumable film has mucoadhesive properties and a minimum dissolution time of at least a few minutes; and
 (iii) a package for containing said orally consumable film;
(b) providing indicia identifying the complexate as an active ingredient contained in the packaged pharmaceutical product; and
(c) exposing consumers to the indicia, thereby providing accurate information as to the active ingredient contained in the packaged pharmaceutical product.

* * * * *